(12) United States Patent
Sapp, Jr. et al.

(10) Patent No.: US 10,039,454 B2
(45) Date of Patent: Aug. 7, 2018

(54) COMPUTER-AIDED LOCALIZATION OF SITE OF ORIGIN OF CARDIAC ACTIVATION

(75) Inventors: John Lewis Sapp, Jr., Halifax (CA); Bohumil Milan Horacek, Halifax (CA); Ahmed Mohamed Fahmey El-Damaty, Halifax (CA)

(73) Assignee: Dalhousie University, Halifax (CA)

( * ) Notice: Subject to any disclaimer, the term of this patent is extended or adjusted under 35 U.S.C. 154(b) by 598 days.

(21) Appl. No.: 14/128,842

(22) PCT Filed: Jun. 20, 2012

(86) PCT No.: PCT/CA2012/050410
§ 371 (c)(1),
(2), (4) Date: Feb. 6, 2014

(87) PCT Pub. No.: WO2012/174660
PCT Pub. Date: Dec. 27, 2012

(65) Prior Publication Data
US 2014/0163395 A1 Jun. 12, 2014

Related U.S. Application Data (60) Provisional application No. 61/501,036, filed on Jun. 24, 2011.

(51) Int. Cl.
*A61B 5/0205* (2006.01)
*A61B 5/0402* (2006.01)
(Continued)

(52) U.S. Cl.
CPC .......... *A61B 5/0205* (2013.01); *A61B 5/0402* (2013.01); *A61B 5/04085* (2013.01); *A61B 5/7246* (2013.01); *A61N 1/362* (2013.01)

(58) Field of Classification Search
CPC . A61B 5/0205; A61B 5/0402; A61B 5/04085; A61B 5/7246
(Continued)

(56) References Cited

U.S. PATENT DOCUMENTS 5,103,821 A * 4/1992 King .................. A61F 2/00 600/36
6,493,575 B1 * 12/2002 Kesten ............... A61B 90/36 600/431

(Continued)

FOREIGN PATENT DOCUMENTS

| CA | 2600208 | 6/2008 |
|---|---|---|
| WO | 016461 A2 | 10/2001 |
| WO | 2012174660 | 12/2012 |

OTHER PUBLICATIONS

Canadian Intellectual Property Office, International Search Report for PCT Application No. PCT/CA2012/050410, dated Aug. 29, 2012.

(Continued)

*Primary Examiner* — Christopher A Flory
(74) *Attorney, Agent, or Firm* — Hugh Mansfield (57) ABSTRACT

A method for quantifying, during pacemapping, a comparison of a BSPM of interest to a pace site BSPM. The method may include receiving at a computing device a plurality of ECG signals from an acquisition system. The pace site BSPM may be calculated using the plurality of ECG signals. The BSPM of interest may be compared to the pace site BSPM, by: retrieving the BSPM of interest from memory accessible by the computing device; and, calculating one or more comparison metrics for the BSPM of interest as compared to the pace site BSPM. An indication of similarity between the BSPM of interest and the pace site BSPM based (Continued)

on the comparison metric calculated may be displayed on a user interface in communication with the computing device.

10 Claims, 9 Drawing Sheets

(51) Int. Cl.
    *A61B 5/0408*      (2006.01)
    *A61B 5/00*      (2006.01)
    *A61N 1/362*      (2006.01)

(58) Field of Classification Search
    USPC .................................................. 600/483, 509
    See application file for complete search history.

(56) References Cited

U.S. PATENT DOCUMENTS

| | | | |
|---|---|---|---|
| 6,584,343 B1 | 6/2003 | Ransbury et al. | |
| 8,566,375 B1* | 10/2013 | Kerr-Delworth | G06F 17/30289 708/200 |
| 8,620,415 B2* | 12/2013 | Shani | A61B 5/04017 600/509 |
| 8,768,659 B2* | 7/2014 | Vasudevan | G06F 17/18 703/2 |
| 8,934,964 B2* | 1/2015 | Shani | A61B 5/04017 600/509 |
| 2001/0056245 A1* | 12/2001 | Mlynash | A61B 5/04085 600/513 |
| 2001/0056289 A1* | 12/2001 | Sippensgroenewegen | A61B 5/04023 607/5 |
| 2002/0026220 A1* | 2/2002 | Groenewegen | A61B 5/04023 607/4 |
| 2002/0038093 A1 | 3/2002 | Potse et al. | |
| 2002/0065455 A1* | 5/2002 | Ben-Haim | A61B 34/20 600/407 |
| 2002/0165448 A1* | 11/2002 | Ben-Haim | A61B 34/20 600/424 |
| 2004/0015194 A1* | 1/2004 | Ransbury | A61B 5/04023 607/10 |
| 2004/0193223 A1* | 9/2004 | Kramer | A61N 1/3627 607/9 |
| 2005/0182336 A1* | 8/2005 | Sippens Groenewegen | A61B 5/04023 600/518 |
| 2007/0055142 A1* | 3/2007 | Webler | A61B 5/06 600/425 |
| 2007/0167801 A1* | 7/2007 | Webler | G06T 19/00 600/459 |
| 2008/0058657 A1* | 3/2008 | Schwartz | A61B 5/04085 600/508 |
| 2008/0097536 A1* | 4/2008 | Kramer | A61N 1/3627 607/9 |
| 2010/0222671 A1* | 9/2010 | Cohen | G06T 7/0022 600/424 |
| 2010/0228076 A1* | 9/2010 | Blank | G06T 7/0022 600/18 |
| 2010/0290693 A1* | 11/2010 | Cohen | G06T 7/0022 382/134 |
| 2012/0158088 A1* | 6/2012 | Kramer | A61N 1/3627 607/25 |
| 2014/0107510 A1* | 4/2014 | Bogun | A61B 5/0464 600/516 |
| 2014/0161331 A1* | 6/2014 | Cohen | G06T 5/003 382/128 |
| 2014/0323848 A1* | 10/2014 | He | A61B 5/046 600/411 |
| 2015/0282890 A1* | 10/2015 | Cohen | A61B 6/5288 600/424 |
| 2015/0366483 A1* | 12/2015 | Sapp, Jr. | A61B 5/04525 600/523 |

OTHER PUBLICATIONS

The International Bureau, Notification Concerning Submission, Obtention or Transmittal of Priority Document for PCT Application No. PCT/CA2012/050410, dated Aug. 30, 2012.
The International Searching Authority, Notification of Receipt of Search for PCT Application No. PCT/CA2012/050410, dated Jun. 26, 2012.
Gerstenfeld, et al., "Quantitative Comparison of Spontaneous and Paced 12-Lead Electrocardiogram During Right Ventrical Outflow Tract Ventricular Tachycardia", Journal of the American College of Cardiology, vol. 41, No. 11, p. 2046-2053, Jul. 2003 (Jun. 2003).
Kors et al., "Improved Spatial Sampling of ECG Potentials on the Body Surface by Respositioning Electrodes from the standard 12-lead ECG", Computers in Cardiology, vol. 28, pp. 29-32, Sep. 26, 2001.
European Patent Office, Extended European Search Report for European Application No. 12802549.1, dated Dec. 23, 2014. 7 pages.
Aliot et al., EHRA/HRS expert consensus on catheter ablation of ventricular arrhythmias. Heart Rhythm, 6:887-933, 2009.
Arenal et al., Tachycardia-related channel in the scar issue in patients with sustained monomorphic ventricular achycardias: influence of the voltage scar definition. Circulation 2004;110:2568-74.
Bogun et al., Isolated potentials during sinus rhythm and pace-mapping within scars as guides for ablation of post-infarction ventricular tachycardia. J Am Coll Cardiol 2006;47:2013-9.
Harada et al., Catheter ablation of ventricular tachycardia after myocardial infarction: relation of endocardial sinus rhythm late potentials to the reentry circuit. J Am Coll Cardiol 1997;30:1015-23.
Horacek et al., Optimal electrocardiographic leads for detecting acute myocardial ischemia. J Electrocardiol 2001;34 Suppl:97-111.
Hren et al., Value of simulated body surface maps as templates in localizing sites of ectopic activation for radiofrequency ablation. Physiol Meas 1997;18:373-400.
Josephson et al., Ventricular activation during ventricular endocardial pacing. II. Role of pace-mapping to localize origin of ventricular tachycardia. Am J Cardiol 1982;50:11-22.
Josephson et al., Endocardial and epicardial recordings. Correlation of twelve-lead electrocardiograms at the site of origin of ventricular tachycardia. Ann N Y Acad Sci 1990;601:128-47.
Kuchar et al., Electrocardiographic localization of the site of origin of ventricular tachycardia in patients with prior myocardial infarction. J Am Coll Cardiol 1989;13:893-903.
Kuck et al., Catheter ablation of stable ventricular tachycardia before defibrillator implantation in patients with coronary heart disease (VTACH): a multicentre randomised controlled trial. Lancet 2010;375:31-40.
Macleod et al., Validation of an electrocardiographic inverse solution using percutaneous transluminal coronary angioplasty. Annual international conference of the IEEE Engineering in Medicine and Biology Society, vol. 12, No. 2: p. 633-4, 1990.
Miller et al., Relationship between the 12-lead electrocardiogram during ventricular tachycardia and endocardial site of origin in patients with coronary artery disease. Circulation 1988;77:759-66.
Potse et al., Continuous localization of cardiac activation sites using a database of multichannel ECG recordings. IEEE Trans Biomed Eng 2000;47:682-9.
Reddy et al., Prophylactic catheter ablation for the prevention of defibrillator therapy. N Engl J Med 2007:357:2657-65.
Segal et al., A novel algorithm for determining endocardial VT exit site from 12-lead surface ECG characteristics in human, infarct-related ventricular tachycardia. J Cardiovasc Electrophysiol 2007;18:161-8.
Sippensgroenewegen et al., Localization of the site of origin of postinfarction ventricular tachycardia by endocardial pace mapping. Circulation vol. 88, No. 5, Part 1, Nov. 1993.
Sippensgroenewegen et al., Value of body surface mapping in localizing the site of origin of ventricular tachycardia in patients with previous myocardial infarction. J Am Coll Cardiol 1994;24:1708-24.

(56) References Cited

OTHER PUBLICATIONS

Soejima et al., Electrically unexcitable scar mapping based on pacing threshold for identification of the reentry circuit isthmus: Feasibility for guiding ventricular tachycardia ablation. Circulation 2002;106:1678-1683.

Waxman et al., Ventricular activation during ventricular endocardial pacing: I. Electrocardiographic patterns related to the site of pacing. Am J Cariol 1982;50:1-10.

* cited by examiner

COMPUTER-AIDED LOCALIZATION OF SITE OF ORIGIN OF CARDIAC ACTIVATION

FIELD OF THE INVENTION

The present invention relates to computer-aided localization of site of origin of cardiac activation for catheter ablation.

BACKGROUND OF THE INVENTION

Ventricular tachycardia (VT) is one of the most difficult management challenges in clinical cardiac electrophysiology. The spectrum of ventricular arrhythmias spans a wide range of clinical presentations that include premature ventricular complexes (PVCs), non-sustained ventricular tachycardia (NSVT), sustained ventricular tachycardia (VT) and ventricular fibrillation (VF). Any of these presentations can occur in patients with or without structural heart disease. This spectrum applies to any source of tachycardia originating below the His bundle whether from the bundle branches, Purkinje fibers or ventricular myocardium.

VT most commonly occurs in the setting of structural heart disease, such as coronary artery disease, heart failure, cardiomyopathy, congenital heart disease or following cardiac surgery. Prior myocardial infarction (MI) is by far the most common cause of sustained VT. Ventricular tachyarrhythmia associated with MI occurs in two stages. During the acute phase of MI, polymorphic ventricular tachycardia that can degenerate into ventricular fibrillation is most common. On the other hand, sustained monomorphic VT generally arises from the anatomic substrate of a healed MI that usually develops within 2 weeks after an Ml and remains indefinitely. This substrate of healthy and damaged myocardium interlaced with fibrous tissue is found primarily at the border zone of the scar. Fibrosis creates areas of conduction block and increases the separation of myocyte bundles, slowing conduction through myocyte pathways in the border zone of the infarct thus creating a substrate that supports re-entry when an appropriate trigger occurs. With present management of MI, the incidence of sustained post-infarction VT is low, and fewer than 5% of acute MI survivors have inducible ventricular tachycardia when studied early after the acute event. VT exits the scar into the healthy myocardium and depolarizes the myocardium sequentially from this exit site. The location of the exit is responsible for the morphology of the ECG signal.

Sustained monomorphic VT occurring in the absence of structural or electrical heart disease is called idiopathic VT. Idiopathic VT can arise from different sites, but the right ventricular outflow tract (most commonly within 1-2 cm of the pulmonary valve) is by far the most common and accounts for approximately 10% of VTs seen by specialized arrhythmia services. Other potential sites include the left ventricular outflow tract, aortic sinuses of Valsalva (most commonly left) from a crescent of ventricular epicardium underlying the base of the sinus at the aortoventricular junction, in the endocardium adjacent to the mitral annulus and finally from the left ventricular epicardium remote from the sinuses of Valsalva, at sites adjacent to the coronary vasculature. These idiopathic VTs usually have a focal origin caused by triggered activity or abnormal automaticity.

Suppression of VT may be accomplished with the use of implantable cardioverter-defibrillators (ICDs), anti-arrhythmic drugs, arrhythmia surgery and catheter ablation. While antiarrhythmic drugs are considered first line therapy and are commonly used to complement therapy, they are not completely effective in preventing VT episodes and may cause significant cardiac and non-cardiac side-effects. ICD is the only treatment modality that has been demonstrated to offer a significant reduction in mortality in patients with scar-related VT. Although implantable cardioverter-defibrillators (ICDs) can improve the prognosis for patients with VT, recurrent VT can still be life-threatening. Catheter ablation offers a curative treatment for certain types of idiopathic VT and has been suggested to have a benefit for patients who have suffered prior MI in many case studies.

Cardiac mapping refers to all procedures involving recording of body-surface electrocardiograms or endocardial/epicardial electrograms generated due to the spread of the cardiac action potential. This can be recorded from the body surface using either conventional 12-lead electrocardiogram (ECG) or multiple leads (such as for body surface potential mapping (BSPM)), the endocardium or the epicardium. Cardiac mapping provides a means of visualizing the pathophysiological mechanisms underlying ventricular tachycardia, which is crucial for directing catheter ablation procedures.

Several conventional and advanced mapping techniques are frequently utilized to accomplish a successful catheter ablation. However, many of these mapping techniques are hampered by either hemodynamic instability or non-sustained nature of some tachycardias.

Conventional endocardial mapping techniques with catheters placed percutaneously into the heart chambers continue to be the most popular cardiac mapping modality. These catheters are localized and navigated using fluoroscopy. Several conventional mapping techniques have been developed over the last few decades to help understanding the mechanisms of arrhythmias and to guide catheter ablation. These conventional mapping techniques include activation mapping, pacemapping and entrainment mapping.

Pacemapping is a commonly used tool for mapping non-sustained or hemodynamically unstable VT; it is based upon the principle that activation of the heart from a given site will yield a reproducible body surface electrocardiogram (ECG) morphology and that pacing from a site very close to the site at which VT activates the heart (i.e. the site of origin) will result in a matching ECG morphology. However, this technique has some limitations. Comparison of the 12-lead ECG morphology between a pace-map and clinical tachycardia is frequently completely subjective or semi-quantitative. Discrepancies in ablation results may result, in part, from subjective differences in the opinion of a pace-map match to the clinical tachycardia. Another important limitation is that increasing the strength to pace diseased tissues, as in scar-related VT, can excite tissues more distant to the area of stimulation (even if unipolar pacing is used) which may lead to a 12/12 match even 1-1.5 cm away from successful ablation sites. This technique is therefore very time consuming and is limited by imperfect accuracy and spatial resolution, subjectivity of interpretation, and by the need for an intuitive interpretation of the ECG to direct catheter manipulation.

BSPM incorporates data from a much larger number of electrodes, but remains limited by the remote location of the recording site from the cardiac surface resulting in poor spatial resolution of electrical events. The recent development of electrocardiographic imaging (ECGI) represents a further refinement of this technique, combining BSPM and heart torso geometric information to produce detailed electro-anatomical maps of the epicardial surface through application of inverse solution mathematical algorithms. This methodology has permitted accurate localization of focal activation sources, as well as detailed activation sequences during re-entrant arrhythmias. ECGI was recently used to assist in the diagnosis and guiding catheter ablation of focal idiopathic as well as scar related VT. A number of limitations are still under investigation, the most important being the accuracy, but also the complexity of the procedure and the need for a long processing time from electrocardiographic signal acquisition to 3D display of the derived epicardial potentials.

There is therefore a need for a system that assists in the localization of the site of origin.

BRIEF DESCRIPTION OF THE DRAWINGS

In drawings which illustrate by way of example only a preferred embodiment of the invention.

FIG. 8 shows recorded 120-lead QRS integral body surface potential map templates for 16 endocardial segments. The left side of each map corresponds to the front and the right side corresponds to the back of the chest. ECG leads V1-V6 are identified by the black dots. Areas 410 and 400 of the maps represent positive and negative integrals, respectively, whereas the white line 420 marks the zero integral. The locations of the positive/negative extremes (maxima/minima) are indicated by white dots in areas 410 and 400, respectively, and their amplitudes are expressed in mVms in the upper left and upper right of the map respectively. The isointegral lines are separated by automatically determined linear incremental steps that depend on the magnitude of the maxima and the minima and is, for display clarity, restricted to an upper limit of 15 contour lines per map.

DETAILED DESCRIPTION OF THE INVENTION

In one embodiment, there is provided a method for localizing an activation site of origin to a segment of the heart comprising: comparing a body surface potential map (BSPM) of interest to each BSPM template of a pre-determined set of BSPM templates, the set comprising one BSPM template for each pre-defined segment of the heart, wherein the BSPM of interest is calculated based on a plurality of simultaneously recorded electrocardiographic (ECG) signals and wherein comparing comprises, for each BSPM template of the set of BSPM templates: retrieving a BSPM template from memory; and calculating one or more comparison metrics for the BSPM template retrieved as compared to the BSPM of interest, wherein each of the BSPM templates was generated by averaging BSPMs of all pacing sites within the associated segment of the heart from a collection of BSPMs stored in memory; identifying the BSPM template that most closely resembles the BSPM of interest using the comparison metrics calculated in order to identify the segment of the heart in which the activation site of origin is likely to be located.

In further aspects of this embodiment, each of the BSPMs stored in memory represent a pre-determined number of ECG signals; at least one or more estimated BSPMs of the BSPMs stored in memory were calculated from a different number of ECG signals than the pre-determined number; and/or calculation of the one or more estimated BSPMs comprises interpolating between the different number of ECG signals by application of coefficients pre-derived from a collection of BSPMs each representing the pre-determined number of ECG signals.

In another embodiment, there is provided a method for quantifying, during pacemapping, a comparison of a BSPM of interest to a pace site BSPM, the method comprising: receiving at a computing device a plurality of ECG signals from an acquisition system; calculating the pace site BSPM using the plurality of ECG signals; comparing the BSPM of interest to the pace site BSPM, wherein comparing comprises: retrieving the BSPM of interest from memory accessible by the computing device; and calculating one or more comparison metrics for the BSPM of interest as compared to the pace site BSPM; and displaying on a user interface in communication with the computing device an indication of similarity between the BSPM of interest and the pace site BSPM based on the comparison metric calculated.

The present invention provides a system and method for localizing activation sites of origin, such as VT exit site or site of origin. The site of origin may first be localized to a segment or segments of the heart by comparing a BSPM of interest, such as a BSPM calculated from a plurality of ECG signals recorded simultaneously during VT, to BSPM templates, one template for each pre-defined segment of the heart.

Each BSPM template may be derived from a library collection of BSPMs calculated from ECG measurements captured from many patients. The BSPM template for a heart segment may be calculated by computing the mean or average of the corresponding library BSPMs associated with a pacing site within the corresponding heart segment.

The library BSPMs of the collection may each be calculated directly from a predetermined number of previously recorded ECG signals from a patient ("recorded BSPMs"). Where a patient has been measured using a different number of ECG signals, an "estimated BSPM" may be calculated by interpolating between the different number of ECG signals recorded from the patient.

The interpolation may use coefficients, such as regression coefficients, pre-derived from a collection of recorded BSPMs to generate the estimated BSPM from integrals of ECG signals recorded from a different number of ECG signals than the predetermined number of ECG signals used to generate the recorded BSPMs. In an aspect, the different number of ECG signals may comprise a smaller number of ECG signals than the pre-determined number.

In an aspect, the BSPM of interest may also be calculated from a smaller number of ECG signals (i.e., a reduced set of ECG leads) by using either general or patient-specific regression coefficients. Localization of the activation site of origin may be further facilitated during pacemapping by providing an objective measure of the similarity of the BSPM of interest to a pace site BSPM. The similarity between these BSPMs may be quantified by calculating waveform-comparison metrics.

Figure 1:
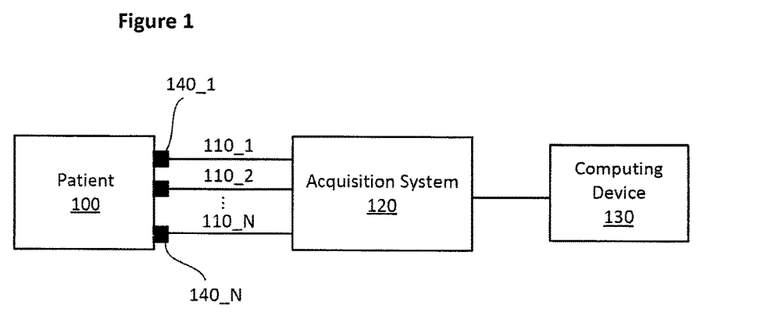
FIG. 1 is a schematic diagram of a computer-aided localization system.
Figure 2:
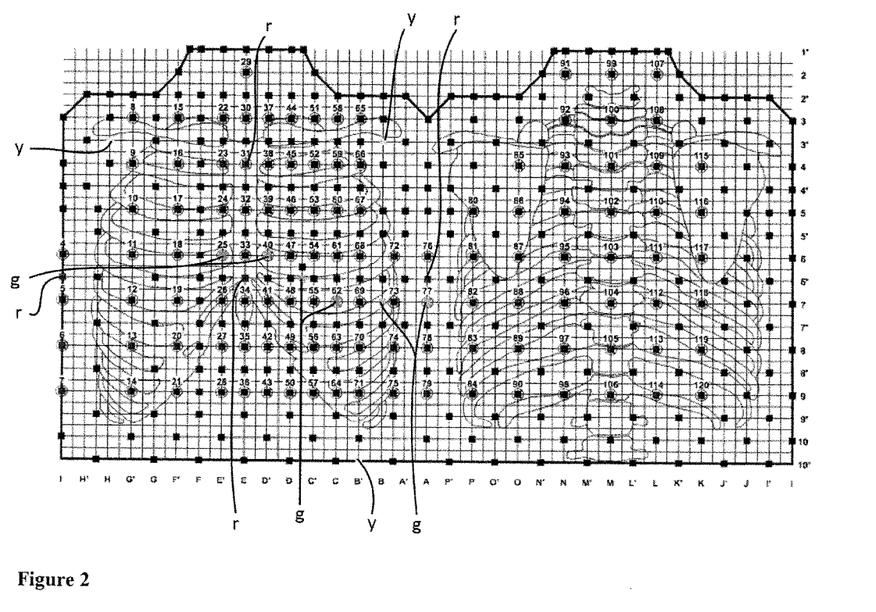
FIG. 2 is a schematic diagram of an arrangement of 120 leads on the torso for body surface potential mapping. The left half of the grid represents anterior surface and right half represents the posterior surface of the chest. Transverse levels (labeled 1', 2 . . . 10') are 1-inch apart from neck to waist; potentials at 352 nodes (unlabelled solid squares) are interpolated from potentials recorded at 120 sites (numbered circles); squares labelled 'g' indicate sites of precordial leads V1-V6; squares labelled 'y' mark sites where electrodes of Mason-Likar substitution for extremity leads are placed; squares labelled 'r' are sites of the EASI leads.

As illustrated in FIG. 1, body surface potentials may be acquired using an acquisition system 120 such as a BioSemi™ Mark-6. An array of electrodes 140_1 . . . 140_N (collectively 140) placed on the patient's torso may be connected via shielded cables or leads 110_1 . . . 110_N to the acquisition system 120. The plurality of surface electrodes 140 may, for example, comprise one hundred and twenty disposable radiolucent Ag/AgCl FoxMed™ surface electrodes. FIG. 2 illustrates one possible arrangement of 120 leads on the torso for body surface potential mapping. Electrocardiographic signals (ECG signals) are simultaneously recorded using Wilson central terminal as reference. The acquisition system 120 may transmit digitized signals to computing device 130, such as a general purpose personal computer, for data display and recording. The signals may be transmitted through a fibre optic cable to the computing device 130. Data may be recorded to memory such as a hard drive of the computer. In one embodiment, the acquisition system 120 samples each channel at at least 250 Hz and preferably at 2000 Hz, and digitizes the ECG signals with at least 16-bit resolution. The analog ECG signals may be amplified and filtered by an antialiasing bandpass filter (e.g., 0.025 to 300 Hz). The raw data files may be recorded for 15-30 seconds during abnormal rhythm, sinus rhythm or paced rhythm. Faulty signals (e.g., due to poor electrode-skin contact, motion artifacts, inaccessibility of the chest area where the electrodes were supposed to be placed, etc.) may be rejected by the operator. ECG signals recorded for BSPMs may include the standard 12 leads and/or the X,Y,Z leads.

The computing device 130 comprises a memory module and/or has access to memory in which the recorded ECG signals, collection of BSPMs, set or library of BSPM templates and/or coefficients for interpolation are stored. The computing device 130 also comprises and/or is in communication with a user interface, such as a display.

Figure 3:
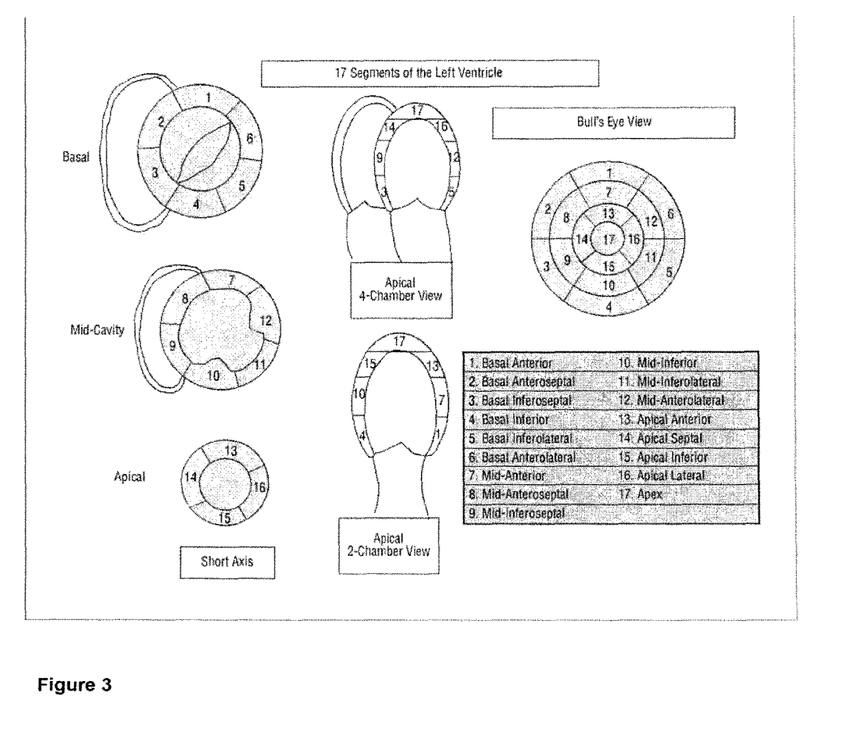
FIG. 3 is an illustration of a 17-segment model of the left ventricle on a circumferential polar plot and the nomenclature for assignments of the CARTO points to anatomical locations. Diagram of vertical long-axis (VLA, 2-chamber view), horizontal long-axis (HLA, 4-chamber view), and short-axis (SA) planes showing the name, location, and anatomic landmarks for selection of the basal, mid-cavity, and apical short axis slices for the recommended 17-segment system.

For activation sites in the left ventricle of the heart, segments of the heart may be defined using electroanatomical maps of the left ventricle. For example, the left ventricle may be divided into 16 segments. The left ventricular cavity may be divided along its longitudinal axis into three equal portions; basal, mid-cavity and apical. The basal and mid portions can be divided into 6 segments. The circumferential segments in the basal and mid-cavity may be anterior, anteroseptal, inferoseptal, inferior, inferolateral and anterolateral. Since the left ventricle tapers as it approaches the apex, the apical segment can be divided to 4 segments only: e.g. apical anterior, apical septal, apical inferior and apical lateral or alternatively, apical anteroseptal, apical inferoseptal, apical anterolateral and apical inferolateral. This 16-segment model is a modification from the 17-segment model of Cerqueira et al. ["Standardized myocardial segmentation and nomenclature for tomographic imaging of the heart", Circulation 2002; 105:539-42] (shown in FIG. 3) due to the absence of an endocardial representative of segment 17 (myocardial cap at the LV apex). The location of each endocardial pacing site or VT origin/exit site may be projected visually from a CARTO™ map to its corresponding location on a polar projection of the left ventricle.

In one embodiment, recorded BSPMs are calculated by selecting a beat from stored recordings of ECG signals and calculating QRS time integrals for each lead. The QRS time integral is calculated for each lead as the algebraic sum of all potentials from the time instant of QRS onset to QRS offset multiplied by the sampling interval. In another embodiment, the time integral may be calculated for a specified duration, such as the initial 100 msec of the QRS.

Estimated BSPMs may be calculated from ECG signals collected through a different number of leads than used for the recorded BSPMs. In an aspect, the different number corresponds to a reduced set of leads. The coefficients used for this calculation may be general regression coefficients derived from a collection or database of BSPMs or, alternatively, patient-specific coefficients derived from BSPMs recorded for the same patient in a pre-procedure session. In another embodiment, data from a set of 32 leads may be used. The anatomical sites for these 32 leads may be pragmatically selected based on accessibility of the sites, coverage of the standard 12-lead and X, Y and Z sites, configuration of available strips of electrodes, etc. Alternatively, sites for a given number of electrodes may be selected that are calculated to be optimal using regression analysis on a collection of BSPMs. As for the recorded BSPMs, the integrals may be calculated for QRS onset to QRS offset or for a specified duration, such as the initial 100 msec of the QRS.

The use of estimated BSPMs greatly simplifies ECG data acquisition during ablation procedure, while maintaining high localization accuracy of BSPMs.

Figure 8:
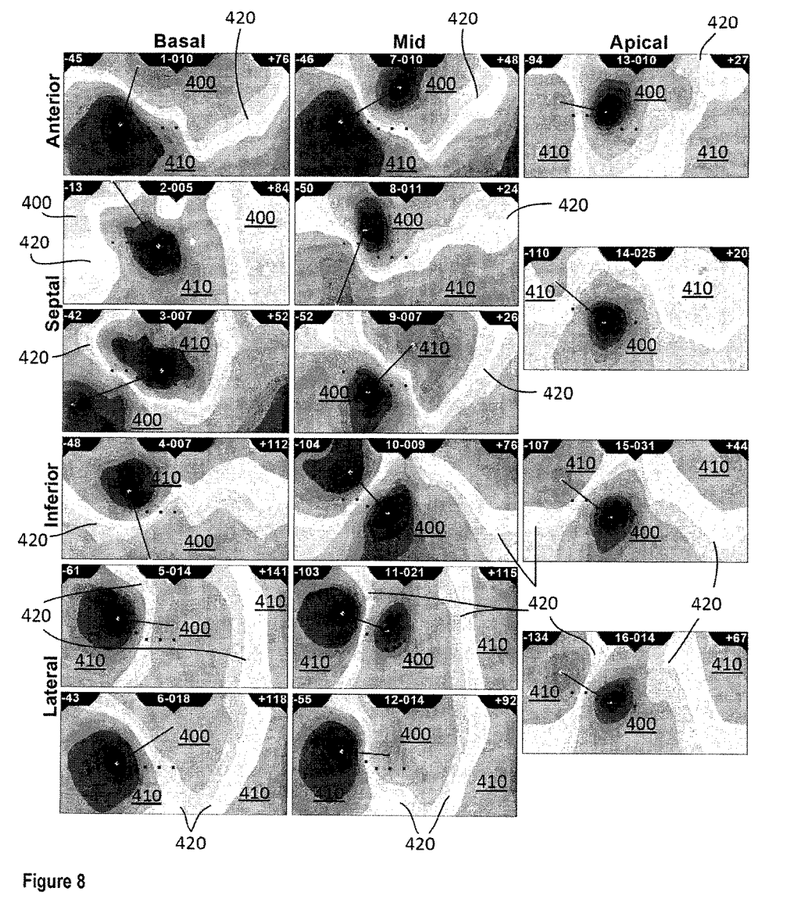
Figure 9:
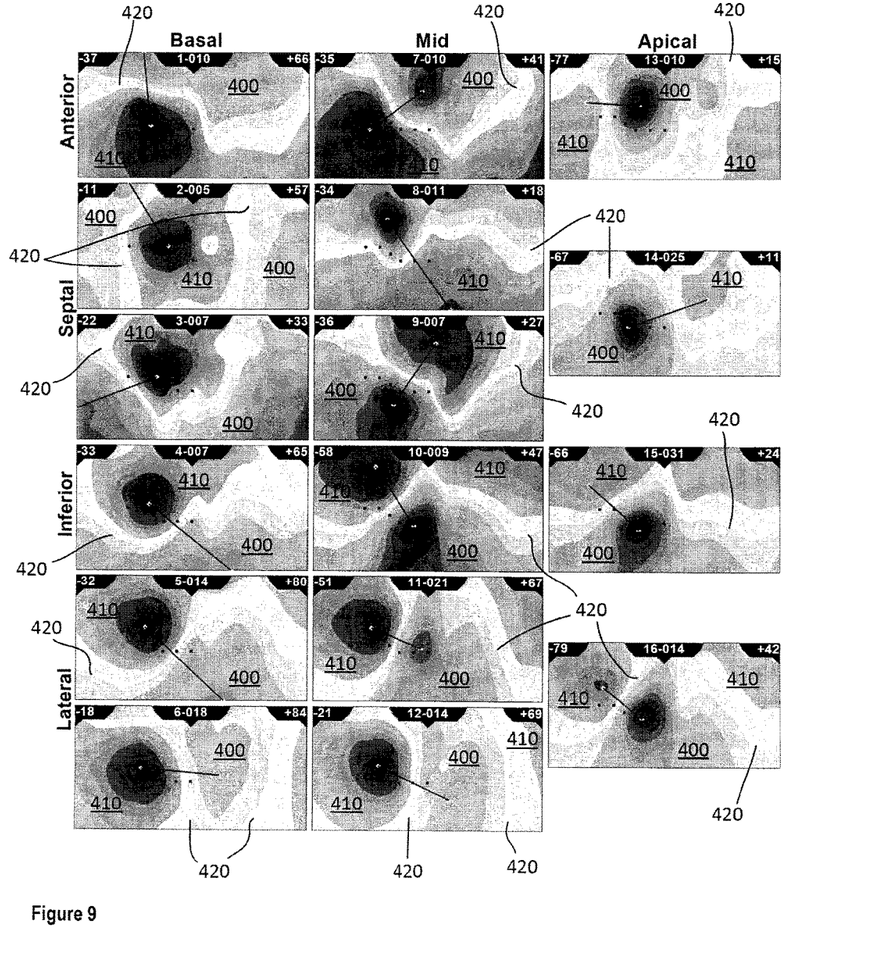
FIG. 9 shows recorded 120-lead 100 msec QRS integral body surface potential map templates for 16 endocardial segments. Note the similar morphology to the QRS BSPM templates with lower amplitudes of the maxima and minima.
Figure 10:
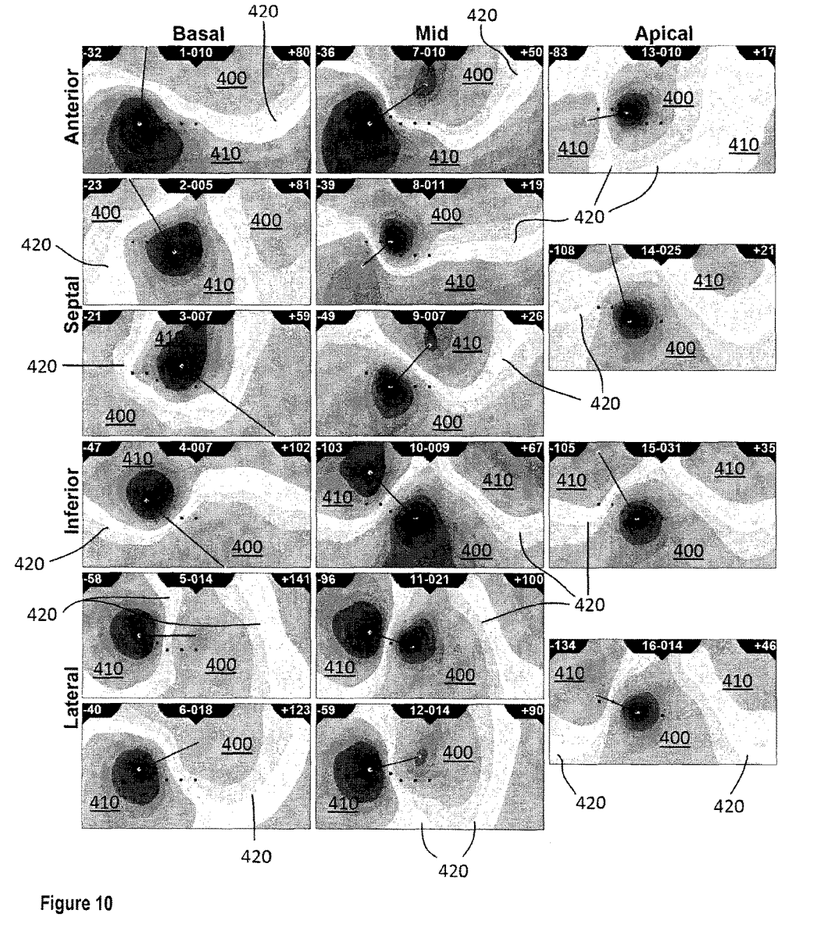
FIG. 10 shows predicted QRS integral BSPM templates from 12-leads ECG by using regression coefficients for 16 endocardial segments. Note the similar morphology to the recorded BSPM and the difference in the values of the maxima and minima.
Figure 11:
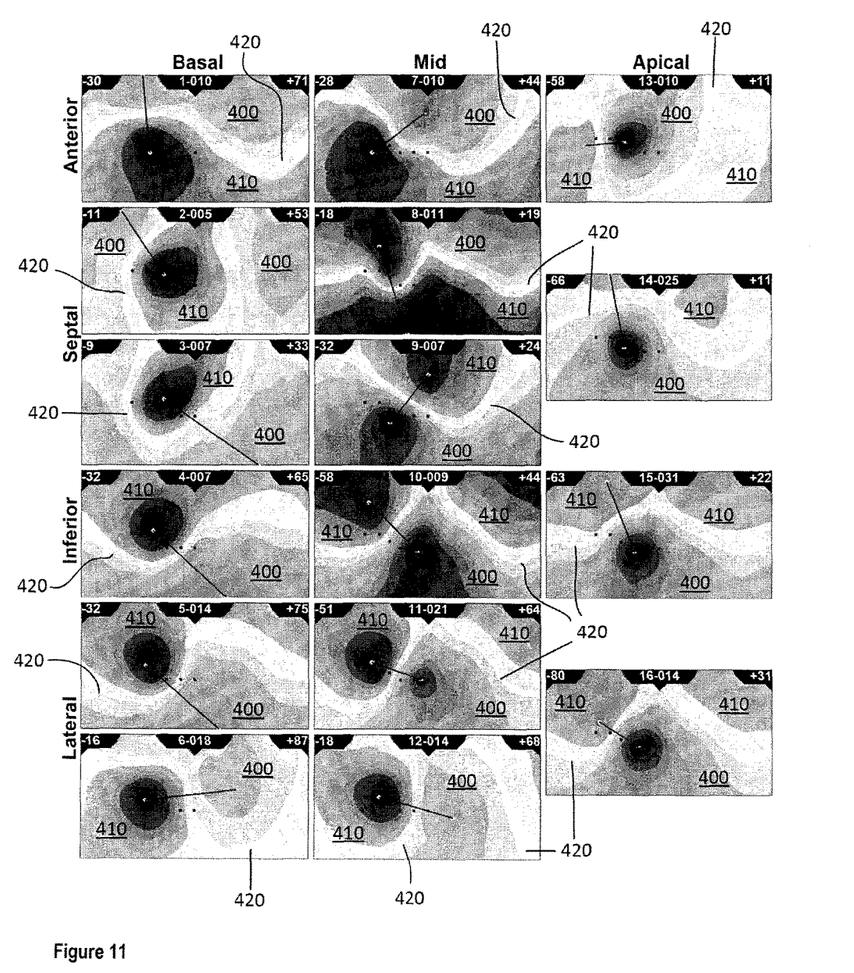
FIG. 11 shows predicted initial 100 msec QRS integral BSPM templates from 12-lead ECG by using regression coefficients for 16 endocardial segments. Note the similar morphology to the recorded BSPM and the difference in the values of the maxima and minima.

BSPM templates or patterns for each segment are calculated by averaging the integrals of all pacing sites within that segment, i.e. averaging all BSPMs for that segment, to obtain a mean BSPM map of the selected interval for each segment. Examples of 120-lead BSPM templates based on recorded BSPMs are shown in FIGS. 8 and 9, FIG. 8 for the interval from QRS onset to QRS offset and FIG. 9 for the initial 100 msec of the QRS. Examples of 120-lead BSPM templates based entirely on BSPMs estimated from the 12-lead ECG by using general regression coefficients are shown in FIGS. 10 and 11, FIG. 10 for the interval from QRS onset to QRS offset and FIG. 11 for the initial 100 msec of the QRS. In the examples of FIGS. 8 to 11, isointegral lines or contours in areas 410 and 400 represent positive and negative integrals, respectively. These areas 410 and 400 are separated by a white line or contour 420 representing the zero integral. In an alternative embodiment, BSPM templates may be based on a combination of recorded BSPMs and estimated BSPMs.

Figure 6:
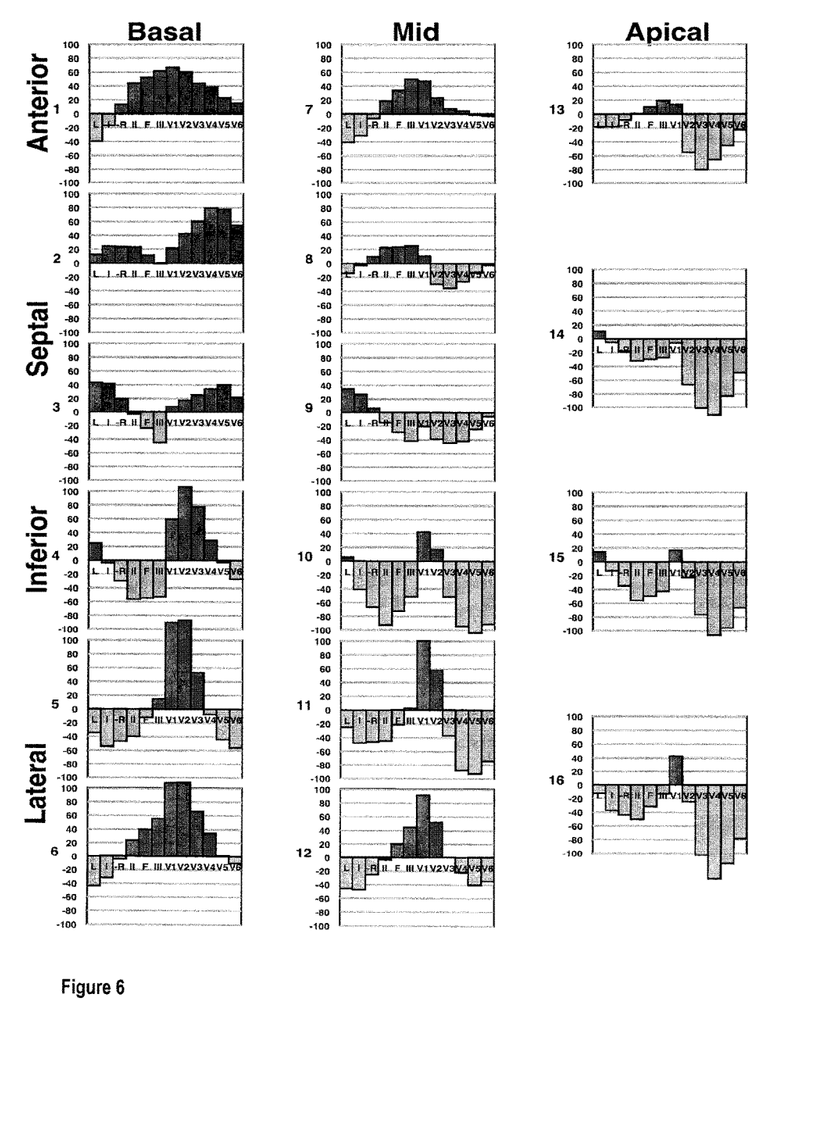
FIG. 6 shows 12-lead QRS integral templates for 16 endocardial segments. ECG leads on the abscissa in each of the 16 panels are ordered in Cabrera sequence (aVL, I, −aVR, II, aVF, III) followed by precordial leads (V1 to V6). Dark-grey (red) bars indicate positive QRS integrals while light-grey (green) bars indicate negative QRS integrals.
Figure 7:
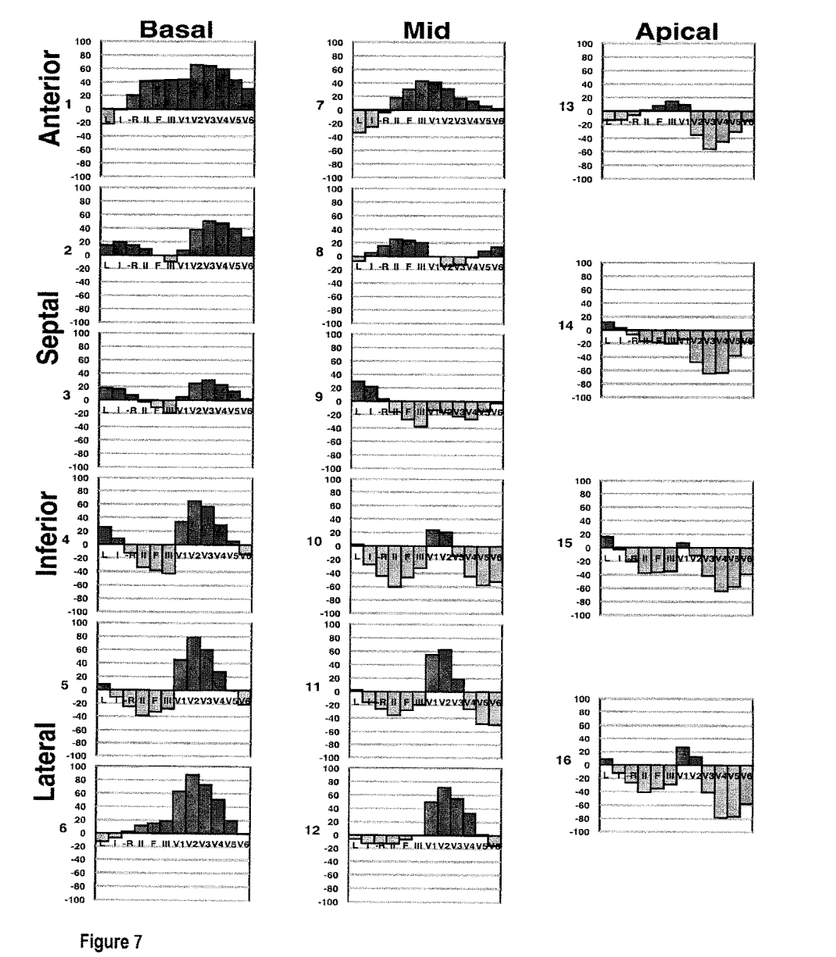
FIG. 7 shows 12-lead 100 msec QRS integral templates for 16 endocardial segments. ECG leads on the abscissa in each of the 16 panels are ordered in Cabrera sequence (aVL, I, −aVR, II, aVF, III) followed by precordial leads (V1 to V6). Dark-grey (red) bars indicate positive QRS integrals while light-grey (green) bars indicate negative QRS integrals.

FIGS. 6 and 7 illustrate 12-lead ECG templates calculated in a similar manner. Although ECG templates for fewer leads such as these may be used to localize activation sites of origin to a segment, localizations may be less accurate than systems that use higher lead count BSPMs.

Figure 4:
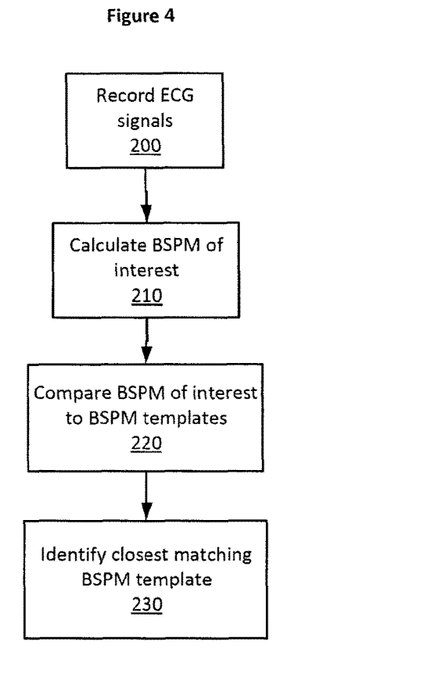
FIG. 4 is a block diagram for identifying the segment of the heart in which the activation site of origin is likely located.

As illustrated in FIG. 4, to localize a site of origin to a segment or group of segments, a plurality of ECG signals are simultaneous recorded at step 200 and a BSPM of interest is calculated at step 210. If the number of ECG signals simultaneously recorded matches the lead count of the BSPM templates, then the BSPM of interest is calculated as described above for recorded BSPMs. If the number of ECG signals simultaneously recorded has a different lead count, for instance is a lower lead count, from the BSPM templates, then the BSPM of interest is calculated as described above for estimated BSPMs. The BSPM of interest is then compared to each BSPM template of a set or library of BSPM templates at step 220. The set of BSPM templates comprises one template for each pre-defined segment of the heart. To quantify the comparison of the BSPM of interest to each of the BSPM templates, the computing device 130 retrieves the BSPM templates stored in memory and at least one waveform comparison metric is calculated for each BSPM template as compared to the BSPM of interest. Examples of waveform comparison metrics that may be used include correlation coefficients, mean absolute deviation and root mean square of the difference. The BSPM template that most closely resembles the BSPM of interest is identified at step 230 using the calculated comparison metrics, e.g., BSPM template associated with the highest correlation coefficient, the lowest mean absolute deviation and/or the lowest root mean square of the difference. As each BSPM template is associated with a particular segment, the site of origin of the BSPM of interest can be localized if not to the identified segment then to the identified segment and segments adjacent to or near the localized segment.

By localizing the site of origin to a region of the heart, the area to be mapped by the operator is limited, thereby reducing the time spent in performing catheter mapping and ablation.

Figure 5:
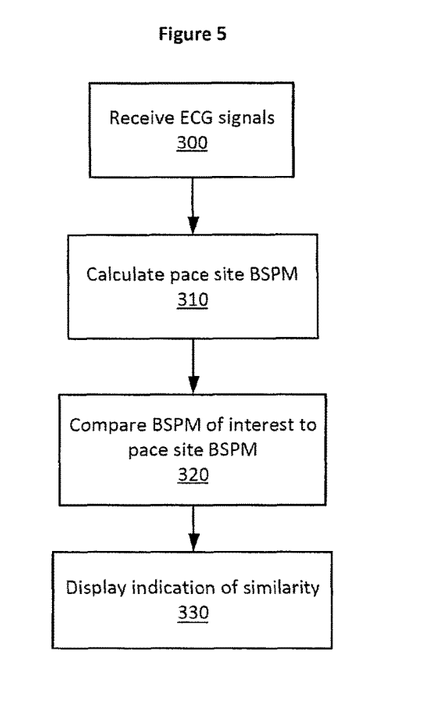
FIG. 5 is a block diagram for displaying an objective measure of the similarity between an BSPM of interest and a pace site BSPM.

As illustrated in FIG. 5, localization of the activation site of origin may be further facilitated during pacemapping by providing an objective measure of the similarity of a pre-recorded BSPM of interest to a pace site BSPM in real-time. In one embodiment, the computing device 130 receives a plurality of simultaneously recorded ECG signals at step 300 associated with a pace site. The computing device 130 then calculates a pace site BSPM at step 310. If the number of ECG signals received matches the lead count of the BSPM of interest, then the pace site BSPM is calculated as described above for recorded BSPMs. If the number of ECG signals received is a different lead count, for instance is a lower lead count, from the BSPM of interest, then the pace site BSPM is calculated as described above for estimated BSPMs. The pace site BSPM is then compared to the BSPM of interest at step 320. To quantify the similarity of the pace site BSPM to the BSPM of interest, the computing device 130 retrieves the BSPM of interest stored in memory and at least one waveform comparison metric is calculated. Examples of waveform comparison metrics that may be calculated include correlation coefficients, mean absolute deviation and root mean square of the difference. An indication of the similarity between the BSPM of interest and the pace site BSPM based on the calculated waveform metric(s) is then displayed on the user interface, such as a computer monitor or screen, in communication with the computing device at step 330.

From various embodiments of the present invention having been thus described in detail by way of example, it will be apparent to those skilled in the art that variations and modifications may be made without departing from the invention. The invention includes all such variations and modifications as fall within the scope of the appended claims.

A portion of the disclosure of this patent document contains material which is subject to copyright protection. The copyright owner has no objection to the facsimile reproduction by any one of the patent document or patent disclosure, as it appears in the Patent and Trademark Office patent file or records, but otherwise reserves all copyrights whatsoever.

We claim:

1. A computer implemented method for localizing an activation site of origin to one of a plurality of segments of the heart comprising:
   acquiring a first plurality of simultaneously recorded electrocardiographic (ECG) signals using a plurality of electrodes,
   calculating a body surface potential map (BSPM) of interest representing a second plurality of ECG signals different than the first plurality from the acquired first plurality of ECG signals by interpolating between the first plurality of ECG signals and the second plurality ECG signals using regression coefficients pre-derived from a collection of previously recorded BSPMs;
   comparing the BSPM of interest to each BSPM template of a pre-determined set of BSPM templates, the set comprising one BSPM template for each pre-defined segment of the heart, wherein the BSPM of interest is calculated from the plurality of simultaneously recorded ECG signals and wherein comparing comprises, for each BSPM template of the set of BSPM templates:
      retrieving a BSPM template from a computer memory; and
      calculating one or more comparison metrics for the BSPM template retrieved as compared to the BSPM of interest,
   wherein each of the BSPM templates was generated by averaging BSPMs of all pacing sites within the associated segment of the heart from a collection of BSPMs stored in computer memory;
   identifying the BSPM template that most closely resembles the BSPM of interest using the one or more comparison metrics calculated in order to identify the segment of the heart in which the activation site of origin is likely to be located; and
   performing catheter mapping on the segment of the heart in which the activation site of origin is likely to be located.

2. The method of claim 1 wherein the BSPM of interest was calculated from a 12 lead ECG.

3. The method of claim 2 further comprising either general or patient-specific coefficients as regression coefficients.

4. The method of claim 1 wherein an optimal number of said second plurality of ECG signals is selected using a regression analysis of the collection of BSPMs.

5. A computer program comprising software code adapted to perform a method for quantifying, during pacemapping, a comparison of a BSPM of interest to a pace site BSPM, the method comprising:
 receiving at a computing device a first plurality of ECG signals from an acquisition system;
 calculating the pace site BSPM in real time using the first plurality of ECG signals, the pace site BSPM representing a second plurality of ECG signals different than the first plurality, by interpolating between the first plurality of ECG signals and the second plurality ECG signals using regression coefficients pre-derived from a collection of previously recorded BSPMs;
 comparing the BSPM of interest to the pace site BSPM in real time, wherein comparing comprises:
 retrieving the BSPM of interest from memory accessible by the computing device; and
 calculating one or more comparison metrics for the BSPM of interest as compared to the pace site BSPM; and
 displaying on a user interface in communication with the computing device an indication of similarity between the BSPM of interest and the pace site BSPM based on the comparison metric calculated.

6. The method of claim 5 further comprising either general or patient-specific coefficients as regression coefficients.

7. The method of claim 5 wherein calculating one or more comparison metrics comprises calculating one or more wave-form comparison metrics.

8. The method of claim 7 wherein the wave-form comparison metrics comprise correlation coefficients, mean absolute deviation and root mean square of the difference.

9. The method of claim 5 further comprising, prior to pace mapping, localizing an activation site of origin to one of a plurality of segments of the heart using said retrieved BSPM of interest.

10. The method of claim 5 wherein an optimal number of said second plurality of ECG signals is selected using a regression analysis of the collection of BSPMs.

* * * * *